United States Patent [19]

Fogel

[11] Patent Number: 5,516,506
[45] Date of Patent: May 14, 1996

[54] EMOLLIENTS FOR SUNSCREENS AND OTHER DERMATOLOGICAL PRODUCTS

[75] Inventor: Arnold W. Fogel, Upper Saddle River, N.J.

[73] Assignee: Bernel Chemical Co., Englewood, N.J.

[21] Appl. No.: 154,523

[22] Filed: Nov. 19, 1993

[51] Int. Cl.$^6$ .................................................... A61K 7/42
[52] U.S. Cl. ........................................................ 424/59
[58] Field of Search ........................................... 424/59

[56] References Cited

U.S. PATENT DOCUMENTS 4,940,574  7/1990  Kaplan ...................................... 424/59

OTHER PUBLICATIONS

Chem. Abs. 19, vol. 111:140187, (Abs. of Jpn. Kokai 01066107), Mar. 1989 Mori et al.
Chem. Abs., 19, vol. 111:83886 (Abs. of Jpn. Kokai 63302935), Dec. 1988, Yamamoto.
Chem. Abs., 19, vol. 95:192204 (Abs. of Jpn. 56097210), Aug. 1981, Shiseido.
Chem. Abs., 19, vol. 84:8857, (Abs. of Jpn. Kokai 50121442) Sep. 1975.
Derwent Abstract of Japanese Pat 58140007, Aug. 19, 1983.
Chem. Abs., 19, vol. 107:96342 (Abstract of JP 62056452) (Mar. 12, 1987), Maeda et al.
Chem. Abs., 19, vol. 113:197680 (Abs. of Jpn. Kokai 02129110) (May 17, 1990), Mori.
Chem. Abs., 19, vol. 111:140220 (Abstr. of Jpn. Kokai 01019012), (Jan. 23, 1990).

*Primary Examiner*—Shelley A. Dodson
*Attorney, Agent, or Firm*—Anthony D. Cipollone

[57] ABSTRACT

Two specific diesters of neopentyl glycol used in varying combinations are introduced as replacements for mineral oil in cosmetic formulations which increases SPF of the formulations, are unusually safe even when used neat, have zero comedogenicity and mimic mineral oil in all of its good physical and chemical properties.

8 Claims, No Drawings

EMOLLIENTS FOR SUNSCREENS AND OTHER DERMATOLOGICAL PRODUCTS

BACKGROUND OF THE INVENTION

There has been a movement in cosmetic chemistry recently to seek a replacement for mineral oil in cosmetic formulations.

The synthetic ester that replaces mineral oil entails discovery of an ester with emollient properties yet to be seen in any synthetic ester that does not adversely affect SPF. In fact, the reverse is true, the esters enhance SPF.

In evaluating emolliency, reference is made to the initial rubout feel on the skin followed by testing 15 minutes later, 1 hour later and 2 hours later.

What makes mineral oil so unique is the fact that the emollient, that is, the mineral oil, stays on top of the skin.

Presently, your Petitioner has been granted U.S. Pat. No. 5,116,604, Trade Name, Elefac®, which introduces a unique neopentanoate ester having the following structure:

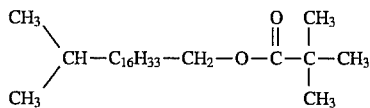

This ester has extraordinary emolliency that significantly enhances the sun protective factor (SPF) of a sunscreen formulation. In addition, it has these desirable properties: clear, low-freezing liquid, good color, odor, non-comedogenicity, stable and safe. It is also a moisturizer and pigment wetter for cosmetic products. However, this Elefac® does not match the emolliency of mineral oil.

The instant presentation is the end result of a continuous pursuit of excellence by the Petitioner in the cosmetic chemistry field. It is a mineral oil substitute and SPF booster. Since mineral oil is so prevalent as an emollient in the cosmetic industry, great effort has been expended in the present invention. The intense effort is caused by the cosmetic Formulators' desire to delete mineral oil from their formulations.

The Petitioner has developed and discovered an emollient combination which mimics mineral oil in all of its good properties both physical and chemical and does not exhibit any of the negative mineral oil properties that have led to a search for its replacement in cosmetic formulations. The instant invention when used in cosmetic formulations increases the SPF of the end product, is unusually safe even when used neat and has zero comedogenicity.

The introduction of the esters and their combination herein presented eliminates all of the problems associated with mineral oil in cosmetic formulations.

DESCRIPTION OF PRIOR ART

U.S. Pat. No. 4,264,581 describes an improved composition containing the active ingredients 2-ethylhexyl-N N-dimethyl-p-aminobenzoic acid and 2-hydroxy-4-methoxy benzophenone.

U.S. Pat. No. 4,224,311 introduces a disubstituted derivative of glycerol employed as an oily excipient in cosmetic compositions.

U.S. Pat. No. 4,940,577 presents a cosmetic composition comprising an ester containing emulsion with a minor amount of water. This composition is a clear, water-in-ester microemulsion.

U.S. Pat. No. 4,908,355 teaches a method of treating skin disorders such as acne vulgaris.

U.S. Pat. No. 5,238,965 relates to methods of regulating wrinkles in mammalian skin comprising topical application of a lysophosphatidic acid compound.

OBJECT OF THE INVENTION

It is the object of this invention to introduce the novel use of two specific diesters of neopentyl glycol to replace mineral oil in cosmetic formulations. Unlike mineral oil which decreases SPF, the diesters introduced for this application increase SPF, exhibit none of the drawbacks of mineral oil and are unusually safe even when used neat and are non-comedogenetic. These diesters in varying combinations may also be used as wetting, dispersing and cleansing agents for pigmented products.

SUMMARY AND DESCRIPTION OF THE INVENTION

Neopentyl glycol reacts with isostearic acid and 2-ethyl hexanoic acid to produce the neopentyl glycol diesters as follows:

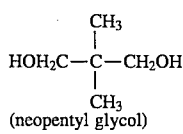
(neopentyl glycol)    I

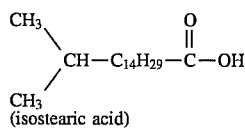
(isostearic acid)    II

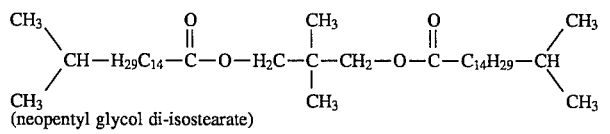
(neopentyl glycol di-isostearate)    III

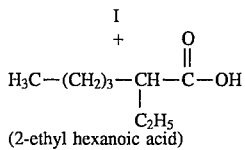
(2-ethyl hexanoic acid)

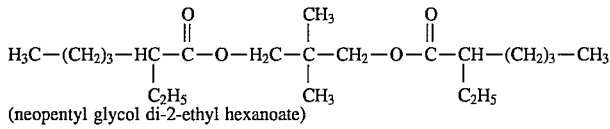
(neopentyl glycol di-2-ethyl hexanoate)

A blend of III & V diesters in varying proportions introduces a novel use of these diesters to give cosmetic formulations their unique properties.

The following blends are the preferred embodiments of the invention:

A. 90% III & 10% V produces a composition which exactly mimics mineral oil in all its preferred properties and additionally increases SPF.

B. 90% V & 10% III gives a drier feel and not as oily, much like the neopentanoate ester Elefac.

A 50/50 blend of A & B gives the benefits of both A & B equally.

Following are sample formulations:

WATERPROOF SUNSCREEN EMULSION*

PHASE A (85° C.)

| | | |
|---|---|---|
| | Water, Deionized | 47.70% to 72.70% (range-Q.S. 100.0%) |
| | Glycerine | 4.00 |

PHASE B (Dry Blend)

| | | |
|---|---|---|
| (1) | Veegum ® | 0.75 |
| (2) | Keltrol ® | 0.25 |

PHASE C (85° C. - Mix and Dissolve)

| | | |
|---|---|---|
| (3) | Isostearic Acid (Emersol 875) | 4.00 |
| (3) | Cetyl Alcohol | 1.00 |
| (8) | Amphisol | 2.00 |
| (5) | Minno ™ 41 | 5.0% to 30.0% (range) |
| (4) | D.C. Silicone Fluid 200 (100cs) | 0.50 |
| (9) | Parsol MCX | 7.50 |
| (10) | Parsol 1789 | 2.00 |
| | Methyl Paraben | 0.20 |
| | Propyl Paraben | 0.10 |
| | | 100.00% TOTAL |

PROCEDURE
Add Phase B to Phase A and mix until uniform and "smooth". Hold 85° C., then add Phase C. Mix until uniform. Cool and mix to 30° C. Package.
SUPPLIERS:
(1) R. T. Vanderbilt
(2) Kelco, Div. Merck
(3) Emery/Henkel
(4) Dow Corning
(5) Minno ™ 41 = (90% III + 10% V)
(6) Veegum ® - Magnesium Aluminum Silicate
(7) Keltrol ® - Xanthan Gum
(8) Amphisol - DEA cetylphosphate
(9) Parsol MCX - Octyl methoxy cinnamate
(10) Parsol 1789 - butyl methoxy dibenzoylmethane
*SPF mean of 20 people = 17

WATER-PROOF SUNSCREEN OIL FORMULATION*

| | | |
|---|---|---|
| (1) | Isostearic Acid (Emersol 875) | 4.00 |
| (1) | Isocetyl Alcohol | 1.00 |
| (3) | Minno ™ 41 | 5.0% to 30.0% (range) |
| (4) | Hetester ® PMA | 15.00 |
| (2) | D.C. Volatile Silicone 344 | 25.00 |
| | Parsol MCX | 7.50 |
| | Parsol 1789 | 2.00 |
| | SD 40 Ethanol (Anhydrous) | 15.5 to 40.50 (range - Q.S. to 100.0%) |
| | | 100.00% TOTAL |

PROCEDURE
Mix all together at room temperature. Warm to 45° C., mix until all dissolves. Cool to 30° C. Package.
SUPPLIERS:
(1) Emery/Henkel
(2) Dow Corning
(3) Minno ™ 41 (90% III + 10% V)
(4) Hetester ® PMA - Propylene glycol myristyl ether acetate
*SPF mean of 20 people = 16

SUNSCREEN LOTION*

PHASE A (45° C.)

| | | |
|---|---|---|
| | Water, Deionized | 52.2 to 72.2 (range - Q.S. 100.0) |

PHASE B (Dry Blend)

| | | |
|---|---|---|
| (1) | Carbopol 940 | 0.25 |
| (2) | Veegum | 0.25 |

PHASE C (50° C. - Mix and Dissolve)

| | | |
|---|---|---|
| (6) | Hetester ® PHA | 7.50 |
| (7) | CUPL ® PIC | 5.00 |
| (4) | Minno ™ 41 | 5.0 to 25.0 (range) |
| | Parsol MCX | 7.50 |
| | Parsol 1789 | 2.00 |

PHASE D (Dissolve)

| | | |
|---|---|---|
| | Water Deionized | 2.75 |
| | Triethanolamine, 99% | 0.25 |

PHASE E

| | | |
|---|---|---|
| (3) | Kathon CG | 0.05 |
| | | 100.00% TOTAL |

PROCEDURE
Add Phase B to Phase A, mix until "smooth" and uniform. Then add Phase C, mix well, then add Phase D, then add Phase E. Mix well. Cool to 30° C. Package.
SUPPLIERS:
(1) B. F. Goodrich, Inc.
(2) R. T. Vanderbilt
(3) Methylchloroisothiazolinone and Methylisothiazolinone
(4) Minno ™ 41 (A 90% III + 10% V)
(5) Carbopal 940 - Carbomer 940

SUNSCREEN LOTION*

(6) Hetester ® PHA - Propylene glycol isoceteth-3 acetate
(7) CUPL ® - Dipropylene glycol isoceteth-20 acetate
*SPF mean on twenty (20) people = 17.0

10% UREA CREAM

| PHASE A (Heat to 85° C. and mix until smooth) | |
|---|---|
| (1) Stearic Acid T.P. | 5.00 |
| (2) Cetyl Alcohol | 1.00 |
| (3) Amphisol | 2.00 |
| Minno ™ 41 | 4.00 |
| (8) Minno ™ 21 | 4.00 |
| (4) Silicone Fluid 200 (100cs) | 0.50 |
| PHASE B (Heat to 85° C. and disperse well) | |
| Water, Deionized | 65.65 |
| Glycerine | 5.00 |
| (6) Carbopol | 0.15 |
| PHASE C | |
| (5) Germaben II E | 1.00 |
| PHASE D (Mix) | |
| Water, Deionized | 1.50 |
| Triethanolamine 99% | 0.15 |
| PHASE E | |
| Urea USP | 10.00 |
| PHASE F | |
| (7) Kathon ® CG | 0.05 |
| 100.00% TOTAL | |

Germaben II E — Propylene glycol and diazolidinyl urea (and) methylparaben (and) propylparaben
(8) Minno ™ 21 — (90% V to 10% III)

DISPERSIBLE BATH OIL

| Minno ™ 21 | 40.00 |
|---|---|
| Minno ™ 41 | 40.00 |
| Hetester PHA | 20.00 |
| 100.00% TOTAL | |

PROCEDURE: Mix until clear.

SUNTAN LOTION

| PHASE A 40° C.: Mix until dispersed. | |
|---|---|
| Hetester ® PHA | 10.00 |
| CUPL PIC ™ | 2.00 |
| Minno ™ 21 | 5.0 to 40.0 (range) |
| TiO₂ (Micronized) | 9.00 |
| ZnO (Micronized) | 3.00 |
| PHASE B (40° C.) | |
| Water, deionized | 34.9 to 69.9 (range-Q.S. to 100.0) |
| PHASE C (Dry Blend) | |
| Veegum ® | 0.70 |
| Keltrol ® | 0.30 |
| PHASE D | |
| Kathon ® CG | 0.10 |
| 100.00% TOTAL | |

SUNTAN LOTION

PROCEDURE:
Add Phase C to Phase B and mix until "smooth". Then, with proper mixing (propeller causing a vortex), add Phase A. Mix until uniform and add Phase D. Mix until uniform.

What is claimed is:

1. A water proof sunscreen emulsion composition containing from 47.70% to 72.70% water, 4.0% glycerine, 0.75% magnesium aluminum silicate, 0.25% xanthan gum, 2.00% DEA-cetylphosphate, 4.00% isostearic acid, 0.50% silicone fluid 200 cs., 7.50% octyl methoxy cinnamate, 2.00% butyl methoxy dibenzoylmethane, 0.20% methyl and 0.10% propyl paraben and an emollient component comprising of two neopentyl glycol diesters, neopentyl glycol-2-ethyl hexanoate and neopentyl glycol di-isostearate which vary in weight/weight ratio from $$\frac{90\% \text{ neopentyl glycol di-2-ethyl hexanoate}}{10\% \text{ neopentyl glycol di-isostearate}}$$

to $$\frac{10\% \text{ neopentyl glycol di-2-ethyl hexanoate}}{90\% \text{ neopentyl glycol di-isostearate}}$$

said emollient component serving to enhance SPF and give the desired properties of mineral oil, said emollient component ranging from 5.0% to 30.0% by weight of finished composition.

2. The said sunscreen emulsion compositon in claim 1 wherein the said emollient component is $$\frac{10\% \text{ neopentyl glycol di-2-ethyl hexanoate}}{90\% \text{ neopentyl glycol di-isostearate}}.$$

3. A water proof sunscreen oil composition containing 4.00% isostearic acid, 1.00% isocetyl alcohol, 15.00% propylene glycol myristyl ether acetate, 25.0% volatile silicone, 7.50% octyl methoxy cinnamate, 2.00% butyl methoxydibenzoylmethane, from 15.5 to 40.50% anhydrous ethanol and an emollient component comprising of two neopentyl glycol diesters, neopentyl glycol-2-ethyl hexanoate and neopentyl glycol di-isostearate which vary in weight/weight ratio from $$\frac{90\% \text{ neopentyl glycol di-2-ethyl hexanoate}}{10\% \text{ neopentyl glycol di-isostearate}}$$

to $$\frac{10\% \text{ neopentyl glycol di-2-ethyl hexanoate}}{90\% \text{ neopentyl glycol di-isostearate}}$$

said emollient component serving to enhance SPF and give the desired properties of mineral oil, said emollient component ranging from 5.0% to 30.0% by weight of the finished composition.

4. The said water-proof sunscreen oil composition in claim 3 wherein the said emollient component is $$\frac{10\% \text{ neopentyl glycol di-2-ethyl hexanoate}}{90\% \text{ neopentyl glycol di-isostearate}}.$$

5. A sunscreen lotion composition containing from 52.20%, 72.20% water, 0.25% carbomer 940, 0.25% magnesium aluminum silicate, 7.50% propylene glycol isoceteth-3 acetate, 5.00% dipropylene glycol isoceteth-20 acetate, 7.50% octyl methoxy cinnamate, 2.00% butyl methoxy dibenzoylmethane, 0.25% triethanolamine, 0.05% methylchloroisothiazolinone (and) methylisothiazolinone and an emollient component comprising of two neopentyl glycol diesters, neopentyl glycol di-2-ethyl hexanoate and neopentyl glycol di-isostearate which vary in weight/weight ratio from 90% neopentyl glycol di-2-ethyl hexanoate
10% neopentyl glycol di-isostearate to 10% neopentyl glycol di-2-ethyl hexanoate
90% neopentyl glycol di-isostearate said emollient component serving to enhance SPF and give the desired properties of mineral oil, said emollient component ranging from 5.0% to 25.0% by weight of the finished composition.

6. The said sunscreen lotion composition in claim 5 wherein the said emollient component is 10% neopentyl glycol di-2-ethyl hexanoate
90% neopentyl glycol di-isostearate 7. A suntan lotion composition comprising 10.0% propylene glycol isoceteth-3-acetate, 2.0% dipropylene glycol isoceteth-20 acetate, 9.0% micronized TiO , 3.0% micronized ZnO, from 34.90% to 69.90% water, 0.30% xanthan gum, 0.70% magnesium aluminum silicate, 0.10% methylchloroisothiazolinone (and) methylisothiazolinone, and an emollient component containing neopentyl glycol di-2-ethyl hexanoate and neopentyl glycol di-isostearate which vary in weight/weight ratio from 90% neopentyl glycol di-2-ethyl hexanoate
10% neopentyl glycol di-isostearate to 10% neopentyl glycol di-2-ethyl hexanoate
90% neopentyl glycol di-isostearate said emollient component serving to give the desired properties of mineral oil, said emollient component ranging from 5.0%–40.0% of said composition.

8. The said suntan lotion composition in claim 9 wherein the said emollient component is 90% neopentyl glycol di-2-ethyl hexanoate
10% neopentyl glycol di-isostearate

\* \* \* \* \*